United States Patent
Trouard et al.

(10) Patent No.: US 10,881,735 B2
(45) Date of Patent: Jan. 5, 2021

(54) PHASE CHANGE NANODROPLET CONJUGATES FOR TARGETED DELIVERY

(71) Applicant: Arizona Board of Regents on Behalf of the University of Arizona, Tucson, AZ (US)

(72) Inventors: Theodore Trouard, Tuczon, AZ (US); Terry Matsunaga, Tucson, AZ (US); Marek Romanowski, Tuczon, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 15/777,496

(22) PCT Filed: Nov. 18, 2016

(86) PCT No.: PCT/US2016/062728
§ 371 (c)(1),
(2) Date: May 18, 2018

(87) PCT Pub. No.: WO2017/087775
PCT Pub. Date: May 26, 2017

(65) Prior Publication Data
US 2018/0344849 A1    Dec. 6, 2018

Related U.S. Application Data

(60) Provisional application No. 62/257,986, filed on Nov. 20, 2015.

(51) Int. Cl.
| | | |
|---|---|---|
| *A61K 9/51* | (2006.01) | |
| *A61K 41/00* | (2020.01) | |
| *A61K 9/107* | (2006.01) | |
| *A61K 9/127* | (2006.01) | |
| *A61K 47/69* | (2017.01) | |
| *A61P 35/00* | (2006.01) | |

(52) U.S. Cl.
CPC .......... *A61K 41/0033* (2013.01); *A61K 9/107* (2013.01); *A61K 9/127* (2013.01); *A61K 41/0028* (2013.01); *A61K 47/6925* (2017.08); *A61P 35/00* (2018.01)

(58) Field of Classification Search
CPC .......... A61K 9/141; A61K 9/143; A61K 9/51; A61K 9/5107; A61K 9/5115; A61K 9/5123; A61K 9/5146; A61K 9/5176
See application file for complete search history.

(56) References Cited

U.S. PATENT DOCUMENTS

| | | | |
|---|---|---|---|
| 4,987,154 A | 1/1991 | Long | |
| 6,416,740 B1 * | 7/2002 | Unger | .................... A61K 9/127 424/450 |
| 6,443,898 B1 | 9/2002 | Unger et al. | |
| 6,676,963 B1 * | 1/2004 | Lanza | .................. A61K 9/1075 424/450 |
| 8,309,129 B2 | 11/2012 | Miller et al. | |
| 2001/0031243 A1 * | 10/2001 | Unger | ................ A61K 41/0028 424/9.51 |
| 2009/0148385 A1 * | 6/2009 | Willard | ................ A61K 49/225 424/9.5 |

OTHER PUBLICATIONS

International Search Report for PCT/US2016/062728 dated Jan. 27, 2017.

\* cited by examiner

*Primary Examiner* — Micah Paul Young
(74) *Attorney, Agent, or Firm* — Thmas Horstemeyer LLP

(57) ABSTRACT

Phase change nanodroplet conjugates and methods of making and using thereof are provided. The phase change nanodroplet conjugates include a nanodroplet having a gaseous precursor on the interior and an outer shell such as a lipid monolayer, a lipid bilayer, or a polymer layer. The phase change nanodroplet conjugates can have one or more nanoparticles attached to the outer layer, e.g. via a linker. The nanoparticles can include therapeutic, prophylactic, or diagnostic nanoparticles. The phase change nanodroplet conjugates can be used for the targeted delivery of a therapeutic, prophylactic, or diagnostic nanoparticle to a target region in a subject in need thereof. The methods can include applying an effective amount of ultrasound radiation to the target region to stimulate vaporization of the gaseous precursor followed by cavitation of the resultant bubble conjugate and release or dispersing of drug or drugs inside the liposomes. Methods of making phase change nanodroplet conjugates are also provided.

19 Claims, 3 Drawing Sheets

2A 2B 3A 3B 3C

PHASE CHANGE NANODROPLET CONJUGATES FOR TARGETED DELIVERY

CROSS-REFERENCE TO RELATED APPLICATIONS

This application is the 35 U.S.C. § 371 national stage application of PCT Application No. PCT/US2016/062728, filed Nov. 18, 2016, where the PCT claims priority to, and the benefit of, U.S. provisional application entitled "PHASE CHANGE NANODROPLET CONJUGATES FOR TARGETED DELIVERY" having Ser. No. 62/257,986, filed Nov. 20, 2015, the contents of which are incorporated by reference in their entireties.

TECHNICAL FIELD

The present disclosure generally relates to nano- and micro-scale particles for targeted delivery of therapeutic, prophylactic, and diagnostic agents.

BACKGROUND

The delivery of a drug to a patient with controlled-release of the active ingredient has been an active area of research for decades. Drug delivery with both targeted and controlled release promises to ultimately reduce drug cytotoxicity and improve drug bioavailability. Currently, the most common approach for targeted release is through micelles, di- or tri block polymeric colloidal core-shell structures, as delivery carriers, where drug molecules are encapsulated in the core and the shell of the colloid is functionalized for specific targets. Although this technique promises targeted delivery, there is no clear mechanism for direct, externally controlled drug release. In fact, because it must maintain stability under physiological conditions, the shell layer of the drug-containing micelle may actually hinder release of the drug from the core or the micelle may break down too early under physiological conditions leading to systemic exposure.

There remains a need for systems and methods that overcome the aforementioned deficiencies.

SUMMARY

In various aspects, phase change nanodroplet conjugates and methods of making and using thereof are provided that overcome the aforementioned deficiencies. The phase change nanodroplet conjugates can be used to controllably and selectively deliver a therapeutic, prophylactic, and/or diagnostic nanoparticle to a target region in a patient in need thereof. In various embodiments, phase change nanodroplet conjugates are provided containing a nanodroplet containing a gaseous precursor and an outer shell encasing the nanodroplet, with a therapeutic, prophylactic, or diagnostic nanoparticle attached to the outer shell. The various phase change nanodroplet conjugate can be in a pharmaceutical formulation with a pharmaceutically acceptable excipient.

In various aspects, the outer shell of the nanodroplet can be a lipid monolayer, a lipid bilayer, or a polymer layer. In some aspects, the outer shell includes a lipid selected from a neutral lipid, a cationic lipid, an anionic lipid, a solid lipid, and a combination thereof.

A variety of nanoparticles can be attached to the outer shell of the nanodroplet. In various aspects, the nanoparticle is a polymeric particle, a lipid particle, a solid lipid particle, an inorganic particle, or a combination thereof.

In various aspects, the gaseous precursor in the nanodroplet includes one of more molecules with a boiling point of −50° C. to 10° C. at standard pressure. The gaseous precursor can be a straight chain or branched chain fluorocarbon, hydrofluorocarbon, or fluorohalocarbon having from 2 to 20 carbon atoms, or a combination thereof. In various aspects, the gaseous precursor is perfluoropropane, perfluorobutane, perfluoropentane, or a combination thereof.

In various embodiments, methods are provided for the targeted delivery of a therapeutic, prophylactic, or diagnostic nanoparticle to a target region in a subject in need thereof. In various embodiments, the methods include administering any one or more of the phase change nanodroplet conjugates or pharmaceutical formulations thereof. The administration can include intravenous administration.

In various aspects, the methods include applying an effective amount of ultrasound radiation to the target region to stimulate vaporization of the gaseous precursor followed by cavitation of the resultant bubble conjugate and release or dispersing of drug or drugs inside the liposomes. The target region can be a specific cell, tissue, organ, or organ system. In various aspects, the target region is the brain. In some aspects, the subject has cancer and the target region is a tumor. The effective amount of ultrasound radiation can be effective to release the therapeutic, prophylactic, or diagnostic agent without damaging the target region.

In various embodiments, methods of making a phase change nanodroplet conjugate are provided. The methods can include reacting a first reactive coupling group on a nanodroplet with a second functional group on a nanoparticle to form a covalent bond conjugating the nanoparticle to the nanodroplet to form the conjugate.

Other systems, methods, features, and advantages of phase change nanodroplet conjugates and methods of making and using thereof will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 3A is a red channel of the fluorescence image demonstrating the location of the rhodamine dye in the lipid. FIG. 3B is a green channel fluorescence image demonstrating the carboxyfluorescein incorporated into the interior of the liposomes. FIG.

3C is a merged image demonstrating the liposomes were successfully conjugated to the outer shell of the microbubble.

Figures 4A, 4B, 4C:
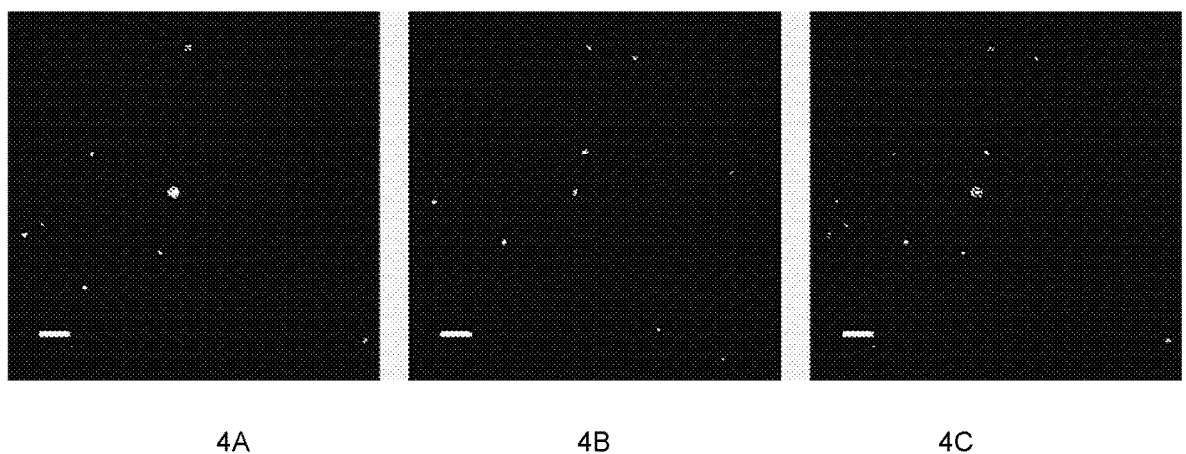

FIGS. 4A-4C demonstrate conjugation of liposomes to the lipid shell surface of a nanodroplet. FIG. 4A is a red channel of the fluorescence image demonstrating the location of the rhodamine dye in the lipid. FIG. 4B is a green channel fluorescence image demonstrating the carboxyfluorescein incorporated into the interior of the liposomes. FIG. 4C is a merged image demonstrating the liposomes were successfully conjugated to the outer shell of the nanodroplet.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, formulations chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The terms "treating" or "preventing", as used herein, can include preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The terms "bioactive agent" and "active agent", as used interchangeably herein, include, without limitation, physiologically, pharmacodynamically, pharmaceutically, pharmacokinetically, or pharmacologically active substances that act locally or systemically in the body. A bioactive agent is a substance used for the treatment (e.g., therapeutic agent), prevention (e.g., prophylactic agent), management, palliation, and/or diagnosis (e.g., diagnostic agent), cure or mitigation of disease or illness, a substance which affects the structure or function of the body, or pro-drugs, which become biologically active or more active after they have been placed in a predetermined physiological environment.

The terms "sufficient" and "effective", as used interchangeably herein, refer to an amount (e.g. mass, volume, dosage, concentration, and/or time period) needed to achieve one or more desired result(s) whether it be suprapharmacologic, for instance, or subpharmacologic and spanning the range in between the two parameters.

The term "biocompatible", as used herein, refers to a material that along with any metabolites or degradation products thereof that are generally non-toxic to the recipient and do not cause any significant adverse effects to the recipient. Generally speaking, biocompatible materials are materials that do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", as used herein, generally refers to the mass or average mass of a molecule making up a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "copolymer" as used herein, generally refers to a single polymeric material that is comprised of two or more different monomers. The copolymer can be of any form, such as random, block, graft, etc. The copolymers can have any end-group, including capped or acid end groups.

The term "hydrophilic", as used herein, refers to substances that have strongly polar groups that are readily soluble in water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties.

The term "mean particle size", as used herein, generally refers to the statistical mean particle size (diameter) of the particles in the composition. The diameter of a spherical or substantially spherical particle may be referred to as the physical or hydrodynamic diameter. The diameter of a non-spherical particle may refer preferentially to the hydrodynamic diameter. As used herein, the diameter of a non-spherical particle may refer to a linear distance between two points on the surface of the particle. Mean particle size can be measured using methods known in the art, such as dynamic light scattering. Two populations can be said to have a "substantially equivalent mean particle size" when the statistical mean particle size of the first population of nanoparticles is within 20% of the statistical mean particle size of the second population of nanoparticles; more preferably within 15%, most preferably within 10%.

The terms "monodisperse" and "homogeneous size distribution", as used interchangeably herein, describe a population of particles, microparticles, or nanoparticles all having the same or nearly the same size. As used herein, a monodisperse distribution refers to particle distributions in which 90% of the distribution lies within 5% of the mean particle size.

The term "targeting moiety", as used herein, refers to a moiety that binds to or localizes to a specific locale. The moiety may be, for example, a protein, nucleic acid, nucleic acid analog, carbohydrate, or small molecule. The locale may be a tissue, a particular cell type, or a subcellular compartment. The targeting moiety or a sufficient plurality of targeting moieties may be used to direct the localization of a particle or an active entity. The active entity may be useful for therapeutic, prophylactic, or diagnostic purposes.

The term "reactive coupling group", as used herein, refers to any chemical functional group capable of reacting with a second functional group to form a covalent bond. The selection of reactive coupling groups is within the ability of the skilled artisan. Examples of reactive coupling groups can include primary amines (—$NH_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes (—COH) and aldehyde reactive linking groups such as hydrazides, alkoxyamines, and primary amines. Examples of reactive coupling groups can include thiol groups (—SH) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The term "protective group", as used herein, refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene, T. W. and Wuts, P. G. M., Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyryl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, 2-(3,5- dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

The term "droplet" as used herein refers to an amount of liquid that is encased or surrounded by a different, enclosing substance (e.g., lipid layer). Droplets that are less than about one micron in size, e.g. about 1.3 μm, 1.2 μm, 1.1 μm, 1.0 μm, 0.9 μm, 0.8 μm, 0.7 μm, 0.6 μm, 0.5 μm, 0.4 μm, 0.3 μm, 0.2 μm, 0.1 μm, or less, are commonly referred to as "nanodroplets".

The term "ultrasound", as used herein, refers generally to acoustic radiation with a frequency greater than about 20 kHz, e.g. about 50 kHz, 100 kHz, 500 kHz, 1,000 kHz, 5,000 kHz, 10,000 kHz, or greater. The ultrasound can be medical ultrasound, e.g. about 500 kHz to 30,000 kHz, about 1,000 kHz to 20,000 kHz, about 2,000 kHz to 15,000 kHz, or about 3,000 kHz to 10,000 kHz.

Discussion

Embodiments of the present disclosure provide for phase change nanodroplet conjugates, methods of making phase change nanodroplet conjugates, methods of targeted delivery of a therapeutic, prophylactic, or diagnostic nanoparticle to a target region using the phase change nanodroplet conjugate, and the like.

Phase change nanodroplet conjugates are provided. The conjugates can have one or a plurality of therapeutic, prophylactic, and/or diagnostic nanoparticles attached covalently or non-covalently to an outer shell encasing a phase change nanodroplet, in some embodiments via a linker. Attaching the therapeutic, prophylactic, targeting moiety and/or diagnostic nanoparticles is advantageous because a greater load can be delivered as compared to using the nanodroplet alone. In addition, embodiments of the present disclosure are stable in the blood stream as compared to microbubble as the microbubble quickly breaks down in the body. Furthermore, a smaller amount of ultrasound energy can be used to release the therapeutic, prophylactic, and/or diagnostic nanoparticles as compared to other technologies.

The conjugates can be used for targeted delivery of the therapeutic, prophylactic, or diagnostic nanoparticle to specific cells, tissues, organs, or organ systems. In some embodiments the conjugates can be used for targeted delivery of the therapeutic, prophylactic, or diagnostic nanoparticle across the blood brain barrier.

The conjugates can have any size, although sizes that will stabilize the particle for circulation in the vasculature without getting metabolized by the reticuloendothelial system (RES) are chosen in some embodiments. The conjugate can have a diameter from about 10 nm to 100 nm, about 20 nm to 100 nm, about 20 nm to 80 nm, about 30 nm to 80 nm, about 100 nm to 10 microns, about 100 nm to 5 microns, about 150 nm to 5 microns, about 150 nm to 2 microns, about 200 nm to 2 microns, about 200 nm to 1.5 microns, about 240 nm to 1.5 microns, about 240 nm to 1.2 microns, about 300 nm to 1.2 microns, about 300 nm to 1 micron, about 400 nm to about 800 nm, or about 500 nm to about 800 nm.

Phase Change Nanodroplet

The conjugates contain a phase change nanodroplet. The phase change nanodroplet can be a liquid at certain temperatures and pressures, but can be stimulated/insonated to form a gas by an appropriate wavelength or wavelengths of ultrasound radiation. The phase change nanodroplet can contain a gas precursor core. The phase change nanodroplet can be encapsulated by an outer shell containing one or more lipids. The gas precursor can be a liquid at certain temperatures and pressures, but can be stimulated to form a gas by an appropriate wavelength or wavelengths of ultrasound radiation.

The phase change nanodroplet can have any size suitable for the intended application. However, in some embodiments the phase change nanodroplet will have a diameter of about 50 nm to 1.5 micron, about 75 nm to 1.5 micron, about 75 nm to 1 micron, about 100 nm to 1 micron, about 150 nm to 1 micron, about 150 nm to 800 micron, about 200 nm to 800 micron, about 200 nm to 500 nm, or about 300 nm to 500 nm.

The phase change nanodroplet can contain a gas precursor. The gas precursor can be selected to have a boiling point such that the gas precursor is a liquid at a specific temperature and pressure when in the nanodroplet, but can be stimulated by radiation to become a gas thereby rupturing or expanding and reorganizing the outer shell encasing the phase change nanodroplet. The gas precursor can have a boiling point temperature of about −50° C. to 10° C., about −40° C. to 10° C., about −30° C. to 10° C., about −20° C. to 10° C., about −10° C. to 10° C., about −10° C. to 5° C., about −8° C. to 5° C., about −8° C. to 0° C., about −5° C. to 0° C., about −2° C. to 0° C., or about −2° C. to −1° C.

The gas precursor can be any molecule having the proper physical properties to be a liquid when encased in the outer shell of the nanodroplet but to be stimulated to a gas by the application of ultrasound frequencies of radiation. The gas precursor can be a fluorocarbon, e.g. a straight chain or branched chain fluorocarbon having from 2 to 20 carbon atoms, from 2 to 12 carbon atoms, from 2 to 10 carbon atoms, from 3 to 10 carbon atoms, from 3 to 8 carbon atoms, or from 3 to 5 carbon atoms. The gas precursor can be a perfluoropropane, perfluorobutane, or perfluoropentane. The gas precursor can be a hydrocarbon, for example a linear or branched hydrocarbon having from 2 to 10 carbon atoms, from 3 to 10 carbon atoms, from 3 to 8 carbon atoms, or from 3 to 5 carbon atoms. The gas precursor can be a hydrofluorocarbon containing one or more hydrogen atoms or other substituents in place of the fluorine. The hydrofluorocarbon can have from 2 to 10 carbon atoms, from 3 to 10 carbon atoms, from 3 to 8 carbon atoms, or from 3 to 5 carbon atoms. The gas precursor can also contain other halofluorocarbon such as those containing chlorine or bromine. The halofluorocarbon can have from 2 to 10 carbon atoms, from 3 to 10 carbon atoms, from 3 to 8 carbon atoms, or from 3 to 5 carbon atoms. The gas precursor can be a mixture of fluorocarbons, hydrocarbons, hydrofluorocarbons, and/or halofluorocarbons.

The phase change nanodroplet can be encased in an outer shell such as lipid monolayer or a lipid bilayer and can be unilamellar or multilamellar. The shell can contain one or more different lipids. For example, the outer shell can contain a neutral lipid, a cationic lipid, an anionic lipid, or a combination thereof. Suitable lipids can include, for example, sterols and lipids such as sterols. cholesterol, phospholipids, lysolipids, lysophospholipids, sphingolipids, ceramides, or pegylated lipids. In some embodiments the outer shell will contain a phospholipid, cholesterol, and a neutral lipid having attached thereto a linker for attaching one or more nanoparticles to the exterior of the phase change nanodroplet shell. In some embodiments one or more of the lipids in the shell will have a reactive coupling group that can be reacted after the phase change nanodroplet is formed to conjugate a nanoparticle to the outer shell of the phase change nanodroplet. The lipid can be DPPC, DMPC, DSPC or other lipids and can have carbon lengths on the fatty acid from about 10-22 carbon atoms. Some drug molecules can also be used as the intercalating agent instead of cholesterol (e.g. rapamycin)

Therapeutic, Prophylactic, and/or Diagnostic Nanoparticles

The conjugate can contain a therapeutic, prophylactic, and/or diagnostic nanoparticle attached covalently or non-covalently to the phase change nanodroplet. The nanoparticle can be attached to the phase change nanodroplet via covalent bonding, ionic bonding, hydrogen bonding, or Van der Waals bonding. The nanoparticle can be attached to the phase change nanodroplet via a linker. In some embodiments the therapeutic, prophylactic, or diagnostic nanoparticle can have a reactive coupling group capable of reacting with a complimentary group on the outer shell of the phase change nanodroplet to form a linker attaching the nanoparticle to the phase change nanodroplet.

The therapeutic, prophylactic, or diagnostic nanoparticle can be a polymeric particle, a lipid particle, a solid lipid particle, an inorganic particle, or combinations thereof. For example, the therapeutic, prophylactic, or diagnostic nanoparticle can be a lipid-stabilized polymeric particle. In some embodiments the therapeutic, prophylactic, or diagnostic nanoparticle is a liposome, a polymeric particle, a solid lipid particle, or a lipid-stabilized polymeric particle.

The therapeutic, prophylactic, or diagnostic nanoparticle may have any diameter. The therapeutic, prophylactic, or diagnostic nanoparticle can have a diameter of about 10 nm to about 10 microns, about 10 nm to about 1 micron, about 10 nm to about 500 nm, about 20 nm to about 500 nm, or about 25 nm to about 250 nm. In some embodiments the therapeutic, prophylactic, or diagnostic nanoparticle has a diameter from about 25 nm to 500 nm, about 50 nm to 500 nm, about 50 nm to 400 nm, about 60 nm to 400 nm, or about 100 nm to 400 nm.

The therapeutic, prophylactic, or diagnostic nanoparticle can have any zeta potential. The therapeutic, prophylactic, or diagnostic nanoparticle can have a zeta potential from −300 mV to +300 mV, −100 mV to +100 mV, from −50 mV to +50 mV, from −40 mV to +40 mV, from −30 mV to +30 mV, from −20 mV to +20 mV, from −10 mV to +10 mV, or from −5 mV to +5 mV. The nanoparticle can have a negative zeta potential. The therapeutic, prophylactic, or diagnostic nanoparticle can have a positive zeta potential. In some embodiments the therapeutic, prophylactic, or diagnostic nanoparticle has a substantially neutral zeta potential, i.e. the zeta potential is approximately 0 mV. In some embodiments the therapeutic, prophylactic, or diagnostic nanoparticle has a zeta potential of approximately −20 mV to +20 mV, more preferably −10 mV to +10 mV.

i. Polymeric Therapeutic, Prophylactic, or Diagnostic Nanoparticles

The therapeutic, prophylactic, or diagnostic nanoparticle can be a polymeric particle. In some embodiments the therapeutic, prophylactic, or diagnostic nanoparticle is a polymeric nanoparticle. Polymeric nanoparticles are known in the art. The polymeric particle can be made from one or a mixture of different polymers that form a polymer matrix. The polymeric nanoparticle is preferably made from one or more biocompatible polymers. The biocompatible polymers can form a biocompatible polymer matrix.

The therapeutic, prophylactic, or diagnostic nanoparticle may be formed from any polymer suitable encapsulation material. The therapeutic, prophylactic, or diagnostic nanoparticle can be formed from biodegradable polymers, non-biodegradable polymers, or a combination thereof. The therapeutic, prophylactic, or diagnostic polymeric nanoparticle can be a biodegradable polymeric nanoparticle in whole or in part. The therapeutic, prophylactic, or diagnostic polymeric nanoparticle can be a non-biodegradable polymeric particle. For example, an imaging agent or diagnostic agent that needs to be retained in the particles and cleared from the body can be encapsulated in a non-biodegradable polymer matrix. In some embodiments, the gas can be used as a diagnostic or therapeutic agent as well since the bubble can be imaged by ultrasound or the bubble can be "popped", possibly inside a cell causing a mini-explosion/implosion to shock or kill the cell from the inside.

The biodegradable therapeutic, prophylactic, or diagnostic nanoparticle can contain one or more biodegradable polymers. The biodegradable polymers can form a biodegradable polymer matrix. Biodegradable polymers can include polymers that are insoluble or sparingly soluble in water that are converted chemically or enzymatically in the body into water-soluble materials. Biodegradable polymers can include soluble polymers crosslinked by hydrolyzable cross-linking groups to render the crosslinked polymer insoluble or sparingly soluble in water.

Biodegradable polymers in the therapeutic, prophylactic, or diagnostic nanoparticle can include polyamides, polycarbonates, polyalkylenes, polyalkylene glycols, polyalkyl glycols polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly (phenyl methacrylate), poly (methyl acrylate), poly(isopropyl acrylate), poly(isobutyl acrylate), poly(octadecyl acrylate), polyethylene, polypropylene poly(ethylene glycol), poly(ethylene oxide), poly (ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly (ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, poly(alkylamines), derivatives thereof, linear and branched copolymers and block copolymers thereof, and blends thereof.

Non-biodegradable polymers can include ethylene vinyl acetate, poly(meth) acrylic acid, polyamides, copolymers and mixtures thereof.

Excipients may also be added to the therapeutic, prophylactic, or diagnostic nanoparticle to alter its porosity, permeability, and or degradation profile.

The therapeutic, prophylactic, or diagnostic polymeric nanoparticle can contain one or more hydrophilic polymers. Hydrophilic polymers include cellulosic polymers such as starch and polysaccharides; hydrophilic polypeptides; poly (amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol), and copolymers thereof.

Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof. In certain embodiments, the hydrophobic polymer is an aliphatic polyester. In preferred embodiments, the hydrophobic polymer is poly(lactic acid), poly(glycolic acid), or poly(lactic acid-co-glycolic acid).

The molecular weight of the hydrophobic polymer can be varied to tailor the properties of the therapeutic, prophylactic, or diagnostic nanoparticle. For example, the molecular weight of the hydrophobic polymer segment can be varied to engineer nanoparticles possessing the required average particle size and degradation profile. The hydrophobic polymer segment has a molecular weight of between about 150 Da and about 100 kDa, more preferably between about 1 kDa and about 75 kDa, most preferably between about 5 kDa and about 50 kDa.

The therapeutic, prophylactic, or diagnostic nanoparticle can contain an amphiphilic polymer. Amphiphilic polymers can include block copolymers of any of the hydrophobic and hydrophilic polymers described above. In some embodiments the amphiphilic polymer is a copolymer containing a hydrophobic polyhydroxyacid block and a hydrophilic polyalkylene glycol block. The amphiphilic polymer can be a PLGA-PEG block copolymer, and PGA-PEG block copolymer, or a PLGA-PEG block copolymer.

The therapeutic, prophylactic, or diagnostic polymeric nanoparticle can contain any of the above polymers or blends or copolymers thereof. The therapeutic, prophylactic, or diagnostic polymeric nanoparticle can contain one, two, three, or more different polymers.

ii. Lipid Therapeutic, Prophylactic, or Diagnostic Nanoparticles

The therapeutic, prophylactic, or diagnostic nanoparticle can be a lipid particle. In some embodiments the therapeutic, prophylactic, or diagnostic nanoparticle is a lipid nanoparticle. Lipid particles and lipid nanoparticles are known in the art. The lipid particles and lipid nanoparticles can be lipid micelles, liposomes, or solid lipid particles. The lipid particle can be made from one or a mixture of different lipids. Lipid particles are formed from one or more lipids, which can be neutral, anionic, or cationic at physiologic pH. The lipid particle is preferably made from one or more biocompatible lipids. The lipid particles may be formed from a combination of more than one lipid, for example, a charged lipid may be combined with a lipid that is non-ionic or uncharged at physiological pH.

The therapeutic, prophylactic, or diagnostic nanoparticle can be a lipid micelle. Lipid micelles for drug delivery are known in the art. Lipid micelles can be formed, for instance, as a water-in-oil emulsion with a lipid surfactant. An emulsion is a blend of two immiscible phases wherein a surfactant is added to stabilize the dispersed droplets. In some embodiments the lipid micelle is a microemulsion. A microemulsion is a thermodynamically stable system composed of at least water, oil and a lipid surfactant producing a transparent and thermodynamically stable system whose droplet size is less than 1 micron, from about 10 nm to about 500 nm, or from about 10 nm to about 250 nm. Lipid micelles are generally useful for encapsulating hydrophobic active agents, including hydrophobic therapeutic agents, hydrophobic prophylactic agents, or hydrophobic diagnostic agents.

The therapeutic, prophylactic, or diagnostic nanoparticle can be a liposome. Liposomes are small vesicles composed of an aqueous medium surrounded by lipids arranged in spherical bilayers. Liposomes can be classified as small unilamellar vesicles, large unilamellar vesicles, or small or large multi-lamellar vesicles. Multi-lamellar liposomes contain multiple concentric lipid bilayers. Liposomes can be used to encapsulate agents, by trapping hydrophilic agents in the aqueous interior or between bilayers, or by trapping hydrophobic agents within the bilayer.

The lipid micelles and liposomes can have an aqueous center. The aqueous center can contain water or a mixture of water and alcohol. Suitable alcohols include, but are not limited to, methanol, ethanol, propanol, (such as isopropanol), butanol (such as n-butanol, isobutanol, sec-butanol, tert-butanol, pentanol (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof. The aqueous center can also contain buffers or even DMSO or DMF.

The therapeutic, prophylactic, or diagnostic nanoparticle can be a solid lipid particle. Solid lipid particles present an alternative to the colloidal micelles and liposomes. Solid lipid particles are typically submicron in size, i.e. from about 10 nm to about 1 micron, from 10 nm to about 500 nm, or from 10 nm to about 250 nm. Solid lipid particles are formed of lipids that are solids at room temperature. They are derived from oil-in-water emulsions, by replacing the liquid oil by a solid lipid.

Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids.

Suitable cationic lipids include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy) propyl]-N,N-dimethyl amine (DODAP), 1,2-diacyloxy-3-dimethylammonium propanes, N-[1-(2,3-dioleyloxy) propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyl trimethyl ammonium bromide (CTAB), $diC_{14}$-amidine, N-ferf-butyl-N'-tetradecyl-3-tetradecylamino-propanamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N, N, N', N'-tetramethyl-, N'-bis(2-hydroxyethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl) imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

Suitable solid lipids include, but are not limited to, higher saturated alcohols, higher fatty acids, sphingolipids, synthetic esters, and mono-, di-, and triglycerides of higher saturated fatty acids. Solid lipids can include aliphatic alcohols having 10-40, preferably 12-30 carbon atoms, such as cetostearyl alcohol. Solid lipids can include higher fatty acids of 10-40, preferably 12-30 carbon atoms, such as stearic acid, palmitic acid, decanoic acid, and behenic acid. Solid lipids can include glycerides, including monoglycerides, diglycerides, and triglycerides of higher saturated fatty acids having 10-40, preferably 12-30 carbon atoms, such as glyceryl monostearate, glycerol behenate, glycerol palmitostearate, glycerol trilaurate, triacetin, tricaprin, trilaurin, trimyristin, tripalmitin, tristearin, and hydrogenated castor oil. Suitable solid lipids can include cetyl palmitate, beeswax, or cyclodextrin.

iii. Inorganic Therapeutic, Prophylactic, or Diagnostic Nanoparticles

The therapeutic, prophylactic, or diagnostic nanoparticle can be an inorganic particle such as metal or semiconductor particles. The nanoparticle can be a metal nanoparticle, a semiconductor nanoparticle, or a core-shell nanoparticle. Inorganic particles and inorganic nanoparticles can be formulated into a variety of shapes such as rods, shells, spheres, and cones. The inorganic particle may have any dimension. The inorganic particle can have a greatest dimension less than 1 micron, from about 10 nm to about 1 micron, from about 10 nm to about 500 nm, or from 10 nm to about 250 nm.

The inorganic particle can contain a metal. Suitable metals can include alkali metals such as lithium, sodium, potassium, rubidium, cesium and francium; alkaline earth metals such as beryllium, magnesium, calcium, strontium, barium and radium; transition metals such as zinc, molybdenum, cadmium, scandium, titanium, vanadium, chromium, manganese, iron, cobalt, nickel, copper, yttrium, zirconium, niobium, technetium, ruthenium, rhodium, palladium, silver, tungsten, iridium, platinum, and gold; post-transition metals such as aluminum, gallium, indium, tin, thallium, lead, and bismuth; lanthanoids such as lanthanum, cerium, neodymium, and europium; and actinoids such as actinium, thorium, protactinium, uranium, neptunium, and plutonium. The metal can be biodegradable or non-biodegradable. Biodegradable metals can include alloys of iron or magnesium with the above metals, including alloys of magnesium, aluminum, and zinc. The metals can include gadolinium, iron, or manganese such as $Gd^{3+}$, $Fe^{3+}$, or $Mn^{2+}$ and can include chelating ligands. The metals can include metals commonly used for imaging, such as those used for MR imaging or PET imaging.

The inorganic particle can contain a metal oxide. Metal oxides of any of the above metals are contemplated. Suitable metal oxides can include metal oxides that contain one or more of the following metals: titanium, scandium, iron, tantalum, cobalt, chromium, manganese, platinum, iridium, niobium, vanadium, zirconium, tungsten, rhodium, ruthenium, gold, copper, zinc, yttrium, molybdenum, technetium, palladium, cadmium, hafnium, rhenium and combinations thereof. Suitable metal oxides can include cerium oxides, platinum oxides, yttrium oxides, tantalum oxides, titanium oxides, zinc oxides, iron oxides, magnesium oxides, aluminum oxides, iridium oxides, niobium oxides, zirconium oxides, tungsten oxides, rhodium oxides, ruthenium oxides, alumina, zirconia, silicone oxides such as silica based glasses and silicon dioxide, or combinations thereof. The metal oxide can be non-biodegradable. The metal oxide can be a biodegradable metal oxide. Biodegradable metal oxides can include silicon oxide, aluminum oxide and zinc oxide.

iv. Hybrid Therapeutic, Prophylactic, or Diagnostic Nanoparticles

The therapeutic, prophylactic, or diagnostic nanoparticle can be a hybrid particle. Hybrid particle, as used herein, refers to a particle that combines the features of two or more of polymeric particles, lipid particles, and inorganic particles. Examples of hybrid particles can include polymer-stabilized liposomes, polymer-coated inorganic particles, or lipid-coated polymeric particles. The hybrid particle can contain a polymeric inner region, a lipid inner region, or an inorganic inner region. The hybrid particle can contain a polymer outer layer, a lipid outer layer, or an inorganic outer layer.

The therapeutic, prophylactic, or diagnostic nanoparticle can be a polymer-stabilized lipid particle. The therapeutic, prophylactic, or diagnostic nanoparticle can be a polymer-stabilized liposome. Polymer-stabilized liposomes are described, for example, in WO 2008/082721 by Dominguez et al. The therapeutic, prophylactic, or diagnostic nanoparticle can be a polymer-stabilized solid lipid particle. Solid lipid particles have been coated with polymers to impart stability (see Nahire et al., *Biomacromolecules* 14:841-853 (2013)) or to impart stealth properties (see Uner and Yener, *Int. J. Nanomedicine* 2:289-300 (2007)). The polymer-stabilized liposomes and polymer-stabilized solid lipid particles include a lipid particle stabilized by the presence of a coating polymer. The coating polymer can be covalently or non-covalently bound to the lipid particle. The coating polymer can be a lipophilic polymer, a biodegradable polymer, a stealth polymer, or a combination thereof.

The therapeutic, prophylactic, or diagnostic nanoparticle can be a polymer-stabilized inorganic particle such as a polymer-coated metal nanoparticle. WO 2013/070653 by Alocilja et al. described metal nanoparticle stabilized by a polysaccharide coating polymer.

Suitable lipophilic polymers can include aliphatic polyesters, such as polylactic acid, polyglycolic acid and their copolymers; poly($\varepsilon$-caprolactone), poly($\delta$-valerolactone), polyesters with longer (i.e., Ci5 to C25) hydrocarbon chains; dendritic polymers of polyesters containing a modified terminal hydroxyl; aliphatic and aromatic polycarbonates; aliphatic polyamides, polypeptides; polyesteramides; polyurethanes; silicones, such as poly(dimethylsiloxanes); lipophilic poly(phosphazenes); poly(methacrylic acid), poly(styrene) and hydrophobic polyacrylic, polyvinyl and polystyrene carriers.

Suitable stealth polymers can include homo polymers or copolymers of polyalkene glycols, such as poly(ethylene glycol), poly(propylene glycol), poly(butylene glycol), and may included acrylates and acrylamide, such as hydroxyethyl methacrylate and hydroxypropylmethacrylamide respectively.

Suitable biodegradable polymers can include polyamides, polycarbonates, saturated polyalkyls, polyalkylenes, polyalkylene glycols, polyalkylene oxides, polyalkylene tereptha-lates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly(ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof. In particularly preferred embodiments the polymeric core contains biodegradable polyesters or polyanhydrides such as poly(lactic acid), poly(glycolic acid), and poly(lactic-co-glycolic acid).

v. Active Agents

The therapeutic, prophylactic, or diagnostic nanoparticles can contain an active agent that has a therapeutic, prophylactic, or diagnostic effect. Any therapeutic, prophylactic, or diagnostic agent can be encapsulated in the nanoparticle. Suitable agents include, but are not limited to, the agents listed below. In some embodiments the nanoparticle has a therapeutic, prophylactic, or diagnostic effect.

The loading range for the agent within the particles is from about 0.01 to about 80% (agent weight/nanoparticle weight), from 0.01% to about 50% (wt/wt), from about 0.01% to about 25% (wt/wt), from about 0.01% to about 10% (wt/wt), or from about 0.1% to about 5% (wt/wt). For small molecules, the percent loading can be from about 0.01% to about 20% (wt/wt), although higher loadings may be achieved for nanoparticles containing agent alone without polymer, lipid, etc. and/or for hydrophobic drugs and/or insoluble metals.

For large biomolecules, such as proteins and nucleic acids, typical loadings are from about 0.01% to about 5% (wt/wt), from about 0.01% to about 2.5% (wt/wt), or from about 0.01% to about 1% (wt/wt). The loading can be calculated relative to the mass of the therapeutic, prophylactic, or diagnostic nanoparticle before attached to the phase change nanodroplet.

The active agent can be a protein or peptide, small molecule, nucleic acid or nucleic acid molecule, lipid, sugar, glycolipid, glycoprotein, lipoprotein, or combination thereof. In some embodiments, the active agent is an antigen or adjuvant, radioactive or imaging agent (e.g., a fluorescent moiety) or polynucleotide. In some embodiments the active agent is an organometallic compound.

Active agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. Active agents can include antibodies and biological products such as such as Herceptin and other MAbs.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eicosanoids (e.g. arachidonic acid, lipoxins, and prostaglandins), and steroid hormones (e.g. estradiol, testosterone, tetrahydro testosterone cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-$\alpha$, IFN-$\beta$, IFN-$\varepsilon$, IFN-$\kappa$, IFN-$\omega$, and IFN-$\gamma$), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammatories (e.g. ibuprofen, naproxen, ketoprofen, and other non-steroidal anti-inflammatories commonly referred to as NSAIDs to one skilled in the art, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravidemtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Linkers

The conjugate can contain a linker attaching one or more nanoparticles to the outer shell of the phase change nanodroplet. For example, a linker can be covalently attached on one end to a nanoparticle and on the opposite end covalently attached to a lipid molecule or other molecule in the outer shell of the phase change nanodroplet. In some embodiments the linker is formed after the nanoparticle and/or the phase change nanodroplet are formed. For example, the linker can be formed by the reaction of a reactive coupling group on the surface of the nanoparticle with a complimentary group on the outer shell of the phase change nanodroplet. In some embodiments the nanoparticle can have a primary amine on the surface and the outer shell of the phase change nanodroplet can have an amine-reactive linking group such as an isocyanate. In some embodiments polymers with reactive coupling groups can be used, e.g. a DSPE PEG 2000-maleimide or DPPE-PEG-2000 PDP. The SPDP can be reduced with a reducing agent to expose the thiolate that reacts with the maleimide to form the conjugate. The conjugates can be prepared with standard solid phase synthesis, e.g. with a soluble carbodiimide (much like peptides, commonly referred to as EDC . . . or the maleimide method). For biologicals that have an exposed lysine, the conjugates can be formed by reacting with iminothiolane (Traut's reagent) followed by reacting with the maleimide. The maleimide can be on the liposome while the thiolate (reduced from the PDP form) can be on the nanodroplet/bubble. In some embodiments, this can also be reversed.

Methods of Making Phase Change Nanodroplet Conjugates

Phase change nanodroplet conjugates can be prepared using synthetic methods known in the art. Representative methodologies for the preparation of phase change nanodroplet conjugates are discussed below. The appropriate route for synthesis of a given phase change nanodroplet conjugate can be determined in view of a number of factors, such as the structure of the phase change nanodroplet conjugates, the composition of the phase change nanodroplet, the composition of the nanoparticles attached to the exterior of the phase change nanodroplet, or the properties of one or more drugs incorporated into the nanoparticles attached to the phase change nanodroplet. In addition to the synthetic methodologies discussed below, alternative reactions and strategies useful for the preparation of the phase change nanodroplet conjugates are known in the art.

A. Phase Change Nanodroplet

Multiple methods of making stable phase change nanodroplets are provided, including phase change nanodroplets with diameters of about 1 micron, 800 nm, 600 nm, 500 nm, 400 nm, 300 nm, 250 nm, or less that contain a gas precursor that can be condensed into the liquid phase in the nanodroplet or cooled and condensed by pressure. The gas precursor can be perfluorocarbons with boiling points that are below body temperature (37° C.) or below room temperature (25° C.), by encapsulating the particles in a lipid, protein, polymer, gel, surfactant, peptide, or sugar. It has been shown that this technique may be used to successfully create stable nanodroplets containing decafluoropentane, octafluoropropane, or a mixture of the two, with and without other substances, where the substance being encapsulated would otherwise vaporize without the stabilizing encapsulation. The nanodroplets so created have activation energies that are low enough that the nanodroplets may be used for human diagnostics, therapeutics, and treatment. The subject matter described herein also includes methods of using these nanodroplets for diagnostics, therapeutics, and other treatments.

The methods can include a process for preparing phase change nanodroplets having a first substance that is enclosed by second substance that acts as an encapsulating material, where the first substance includes at least one component that is a gas at room temperature and atmospheric pressure. Example particles include droplets or emulsions. The gas precursor can be condensed to a liquid phase. This may be done, for example, by cooling the first substance to a temperature below the phase transition temperature of the component having the lowest boiling point, by compressing the first substance to a pressure that is above the phase transition pressure of the component having the highest phase transition pressure, or a combination of the above. The first substance can be extruded into or in the presence of the second substance to create droplets or emulsions in which the first substance is encapsulated by the second substance. The contents of the droplet or emulsion can be entirely or primarily in a liquid phase. The phase change nanodroplets can be extruded at a temperature below the phase transition temperature of the component having the lowest boiling point. In one embodiment, the phase change nanodroplets are formed through a flow-focusing junction in a microfluidic device, where the device is maintained at a temperature below the phase transition temperature of the component having the lowest boiling point. The bubbles can first be made by shaking, followed by temperature/pressure manipulation to condense microbubbles of defined size into nanodroplets.

The phase change nanodroplets can be extruded in a pressurized environment, where the ambient pressure is above the phase transition pressure of the component having the highest phase transition pressure. In one embodiment, the phase change nanodroplets are extruded at a temperature that is either above or below the boiling point of the component having the lowest boiling point. In one embodiment, the phase change nanodroplets are extruded at a temperature that is below the boiling point of the component having the lowest boiling point.

The first substance being encapsulated can include a gas, such as a fluorocarbon, a perfluorocarbon, a chlorofluorocarbon, a hydrofluorocarbon, a hydrocarbon, a gas having a boiling point that is below room temperature (25° C.), or combinations of the above, that is condensed to a liquid phase and encapsulated. The encapsulated droplets can be activatable by exposure to ultrasonic, X-ray, optical, infrared, microwave, or radio frequency energy.

The gas can have a boiling point from about 0° C. to 50° C., 10° C. to 50° C., 10° C. to 40° C., 20° C. to 40° C., or 30° C. to 40° C. at atmospheric pressure. The phase change nanodroplets can be made using a microfluidics technique such as using a flow-focusing junction or a T-junction in a microfluidic device. In one embodiment, the device is maintained at a temperature below the phase transition temperature of the component having the lowest boiling point. The encapsulation material can be a lipid, protein, polymer, gel, surfactant, peptide, or sugar.

The phase change nanodroplets can be made from a first substance extruded into or in the presence of the second substance to create bubbles having an outer shell of the second substance encapsulating an amount of the first substance, at least some of which is in gaseous form. In one embodiment, the contents of the bubble are entirely or primarily in a gaseous phase. The bubble thus formed can be cooled and/or compressed such that the contents of the bubble reach a temperature below the phase transition temperature of the component having the lowest boiling point at that pressure. This causes the gas within the bubble to condense to a liquid phase, which transforms the bubble into a droplet or emulsion. In this manner, droplets or emulsions in which the first substance is encapsulated by the second substance are created. This method offers the advantage of making smaller, more uniform droplet sizes with particle size in the range of about 100 nm to 900 nm, 100 nm to 800 nm, 150 nm to 800 nm, 150 nm to 600 nm, 200 nm to 600 nm, 200 nm to 500 nm, or about 200 nm to 400 nm.

The first substance can include a gas, such as a fluorocarbon, a perfluorocarbon, a chlorofluorocarbon, a hydrofluorocarbon, a hydrocarbon, a gas having a boiling point that is below room temperature (25° C.), or combinations of the above. In one embodiment, the encapsulated droplets are activatable particles by exposure to ultrasonic, X-ray, optical, infrared, microwave, or radio frequency energy.

The gas can have a boiling point from about 0° C. to 50° C., 10° C. to 50° C., 10° C. to 40° C., 20° C. to 40° C., or 30° C. to 40° C. at atmospheric pressure. The phase change nanodroplets can be made using a microfluidics technique such as using a flow-focusing junction or a T-junction in a microfluidic device. In one embodiment, the device is maintained at a temperature below the phase transition temperature of the component having the lowest boiling point. The encapsulation material can be a lipid, protein, polymer, gel, surfactant, peptide, or sugar.

B. Therapeutic, Prophylactic, or Diagnostic Nanoparticles
i. Polymeric Nanoparticles Methods of making polymeric particles are known in the art. Polymeric particles useful as a polymeric nanoparticle can be prepared using any suitable method known in the art. Common microencapsulation techniques include, but are not limited to, spray drying, interfacial polymerization, hot melt encapsulation, phase separation encapsulation (spontaneous emulsion microencapsulation, solvent evaporation microencapsulation, and solvent removal microencapsulation), coacervation, low temperature microsphere formation, and phase inversion nanoencapsulation (PIN). A brief summary of these methods is presented below.

Methods for forming polymeric particles using spray drying techniques are described in U.S. Pat. No. 6,620,617, to Mathiowitz et al. In this method, the polymer is dissolved in an organic solvent such as methylene chloride or in water. A known amount of one or more active agents to be incorporated in the particles is suspended (in the case of an insoluble active agent) or co dissolved (in the case of a soluble active agent) in the polymer solution. The solution or dispersion is pumped through a micronizing nozzle driven by a flow of compressed gas, and the resulting aerosol is suspended in a heated cyclone of air, allowing the solvent to evaporate from the microdroplets, forming particles. Nanospheres as small as about 100 nm can be obtained using this method.

Interfacial polymerization can also be used to encapsulate one or more active agents. Using this method, a monomer and the active agent(s) are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

Nanoparticles can be formed from polymers such as polyesters and polyanhydrides using hot melt microencapsulation methods as described in Mathiowitz et al., Reactive Polymers, 6:275 (1987). In this method, the use of polymers with molecular weights between 3,000-75,000 daltons is preferred. In this method, the polymer first is melted and then mixed with the solid particles of one or more active agents to be incorporated that have been sieved to less than 50 microns. The mixture is suspended in a non-miscible solvent (like silicon oil), and, with continuous stirring, heated to 5° C. above the melting point of the polymer. Once the emulsion is stabilized, it is cooled until the polymer particles solidify.

In phase separation microencapsulation techniques, a polymer solution is stirred, optionally in the presence of one or more active agents to be encapsulated. While continuing to uniformly suspend the material through stirring, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

Methods for forming particles using solvent evaporation techniques are described in E. Mathiowitz et al., J. Scanning Microscopy, 4:329 (1990); L. R. Beck et al., Fertil. Steril., 31:545 (1979); L. R. Beck et al Am J Obstet Gynecol 135(3) (1979); S. Benita et al., J. Pharm. Sci., 73:1721 (1984); and U.S. Pat. No. 3,960,757 to Morishita et al. The polymer is dissolved in a volatile organic solvent, such as methylene chloride. One or more active agents to be incorporated are optionally added to the solution, and the mixture is suspended in an aqueous solution that contains a surface active agent such as poly(vinyl alcohol). The resulting emulsion is stirred until most of the organic solvent evaporated, leaving solid microparticles/nanoparticles. This method is useful for relatively stable polymers like polyesters and polystyrene.

Nanoparticles can also be formed using the phase inversion nanoencapsulation (PIN) method, wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. See, e.g., U.S. Pat. No. 6,143,211 to Mathiowitz, et al. The method can be used to produce monodisperse populations of nanoparticles in a wide range of sizes, including, for example, about 100 nanometers to about 10 microns. Advantageously, an emulsion need not be formed prior to precipitation. The process can be used to form particles from thermoplastic polymers.

ii. Lipid Nanoparticles

Methods of making lipid particles are known in the art. Lipid particles can be lipid micelles, liposomes, or solid lipid particles prepared using any suitable method known in the art. Common techniques for created lipid particles encapsulating an active agent include, but are not limited to high-pressure homogenization techniques, supercritical fluid methods, emulsion methods, solvent diffusion methods, and spray drying. A brief summary of these methods is presented below.

High pressure homogenization is a reliable and powerful technique, which is used for the production of smaller lipid particles with narrow size distributions, including lipid micelles, liposomes, and solid lipid particles. High pressure homogenizers push a liquid with high pressure (100-2000 bar) through a narrow gap (in the range of a few microns). The fluid can contain lipids that are liquid at room temperature or a melt of lipids that are solid at room temperature. The fluid accelerates on a very short distance to very high velocity (over 1000 Km/h). This creates high shear stress and cavitation forces that disrupt the particles, generally down to the submicron range. Generally 5-10% lipid content is used but up to 40% lipid content has also been investigated. Two approaches of HPH are hot homogenization and cold homogenization, work on the same concept of mixing the drug in bulk of lipid solution or melt.

Hot homogenization is carried out at temperatures above the melting point of the lipid and can therefore be regarded as the homogenization of an emulsion. A pre-emulsion of the drug loaded lipid melt and the aqueous emulsifier phase is obtained by a high-shear mixing. HPH of the pre-emulsion is carried out at temperatures above the melting point of the lipid. A number of parameters, including the temperature, pressure, and number of cycles, can be adjusted to produce lipid particles with the desired size. In general, higher temperatures result in lower particle sizes due to the decreased viscosity of the inner phase. However, high temperatures increase the degradation rate of the drug and the carrier. Increasing the homogenization pressure or the number of cycles often results in an increase of the particle size due to high kinetic energy of the particles.

Cold homogenization has been developed as an alternative to hot homogenization. Cold homogenization does not suffer from problems such as temperature-induced drug degradation or drug distribution into the aqueous phase during homogenization. The cold homogenization is particularly useful for solid lipid particles, but can be applied with slight modifications to produce liposomes and lipid micelles. In this technique the drug containing lipid melt is cooled, the solid lipid ground to lipid microparticles and these lipid microparticles are dispersed in a cold surfactant solution yielding a pre-suspension. The pre-suspension is homogenized at or below room temperature, where the gravitation force is strong enough to break the lipid microparticles directly to solid lipid nanoparticles.

Lipid particles, including lipid micelles, liposomes, and solid lipid particles, can be prepared by ultrasonication/high speed homogenization. The combination of both ultrasonication and high speed homogenization is particularly useful for the production of smaller lipid particles. Liposomes are formed in the size range from 10 nm to 200 nm, preferably 50 nm to 100 nm, by this process.

Lipid particles can be prepared by solvent evaporation approaches. The lipophilic material is dissolved in a water-immiscible organic solvent (e.g. cyclohexane) that is emulsified in an aqueous phase. Upon evaporation of the solvent, nanoparticles dispersion is formed by precipitation of the lipid in the aqueous medium. Parameters such as temperature, pressure, choices of solvents can be used to control particle size and distribution. Solvent evaporation rate can be adjusted through increased/reduced pressure or increased/reduced temperature.

Lipid particles can be prepared by solvent emulsification-diffusion methods. The lipid is first dissolved in an organic phase, such as ethanol and acetone. An acidic aqueous phase is used to adjust the zeta potential to induce lipid coacervation. The continuous flow mode allows the continuous diffusion of water and alcohol, reducing lipid solubility, which causes thermodynamic instability and generates liposomes Lipid particles, including liposomes and solid lipid particles, can be prepared from supercritical fluid methods. Supercritical fluid approaches have the advantage of replacing or reducing the amount of the organic solvents used in other preparation methods. The lipids, active agents to be encapsulated, and excipients can be solvated at high pressure in a supercritical solvent. The supercritical solvent is most commonly $CO_2$, although other supercritical solvents are known in the art. To increase solubility of the lipid, a small amount of co-solvent can be used. Ethanol is a common co-solvent, although other small organic solvents that are generally regarded as safe for formulations can be used. The lipid particles, lipid micelles, liposomes, or solid lipid particles can be obtained by expansion of the supercritical solution or by injection into a non-solvent aqueous phase. The particle formation and size distribution can be controlled by adjusting the supercritical solvent, co-solvent, non-solvent, temperatures, pressures, etc. Lipids can also be dissolved in propylene glycol followed by reconstitution and heating. Then the lipids can be shaken with a modified dental amalgamator (shaker).

Microemulsion based methods for making lipid particles are known in the art. These methods are based upon the dilution of a multiphase, usually two-phase, system. Emulsion methods for the production of lipid particles generally involve the formation of a water-in-oil emulsion through the addition of a small amount of aqueous media to a larger volume of immiscible organic solution containing the lipid. The mixture is agitated to disperse the aqueous media as tiny droplets throughout the organic solvent and the lipid aligns itself into a monolayer at the boundary between the organic and aqueous phases. The size of the droplets is controlled by pressure, temperature, the agitation applied and the amount of lipid present.

The water-in-oil emulsion can be transformed into a liposomal suspension through the formation of a double emulsion. In a double emulsion, the organic solution containing the water droplets is added to a large volume of aqueous media and agitated, producing a water-in-oil-in-water emulsion. The size and type of lipid particle formed can be controlled by the choice of and amount of lipid, temperature, pressure, co-surfactants, solvents, etc.

iii. Inorganic Nanoparticles

Methods of making inorganic particles are known in the art. Inorganic particles useful as therapeutic, prophylactic, or diagnostic nanoparticle can be metal particles, semiconductor particles, or metal oxide particles prepared using any suitable method known in the art. Suitable methods of making inorganic particles can include those described in Altavilla, C., and Ciliberto, E., eds. Inorganic Nanoparticles: Synthesis, Applications, and Perspectives. CRC Press, 2010; and Rao et al., *Dalton Trans.* 41:5089-5120 (2012). Common techniques for created inorganic particles include, but are not limited to physical preparation methods, gas-phase and solution-phase chemical preparation methods, and thermolysis methods. A brief summary of these methods is presented below. In some embodiments the inorganic particles encapsulate an active agent. In some embodiments, for example in imaging applications, the inorganic particle is the active agent.

Inorganic particles can be produced by physical preparation methods. Physical preparation methods generally involve the formation of a metal or a metal oxide vapor, typically in a low-pressure or vacuum environment, and coagulation and condensation of particles onto a substrate. The process typically involves use of an inert carrier gas such as He, Ne, or Ar. The heat sources can include electrical sources such as wires or filaments, lasers, or plasma arcs. This is particularly useful for producing elemental particles such as Ag, Fe, Ni, or Ga. Other inorganic particles that can be produced by physical methods can include $TiO_2$, $SiO_2$, and PbS particles. Inorganic particles are often prepared from metal precursors. Metal precursors can include bulk metals, metal halides, metal alkoxides, metal salts, Inorganic particles can be prepared by a variety of chemical preparation methods known in the art. Chemical preparation methods can be conducted in the gas phase or in solution phase. Typically, the monomers used to form the particles are produced by a chemical reaction starting from highly reactive precursors. The reaction may occur spontaneously or may be driven by heat, light, or catalyst.

The inorganic particle can be prepared by reduction of a halide precursor. The basic approach is to have some compound, typically a halide, containing a metal atom, as well as a reducing agent which removes the other parts of the compound. The halide can be F, Cl, Br, or I. An example includes making Mo particles by the reduction of $MoCl_3$, i.e., with $NaBEt_3H$.

The inorganic particles can be prepared by the oxidation of a suitable precursor. For example, $TiO_2$ particles can be prepared by oxidation of the tetrachloride precursor $TiCl_4$. For example, this can be done with an oxygen plasma.

Nanoparticles can also be made by decomposing solid or liquid precursors, often at high temperatures. For example, Li particles can be made by decomposing the solid lithium azide, $LiN_3$. An example occurring at lower temperatures is the formation of gold nanoparticles from a thiolate complex, such as $[C_{14}H_{29}(CH_3)_3N][Au(SC_{12}H_{25})_2]$ which decomposes at 180° C. to produce gold nanoparticles of average size 26 nm that are directly passivated by alkyl groups derived from the precursor complex. [See Nakamoto, *Chem Commun* 15:1622 (2002)]. Al nanoparticles can be made by decomposing $Me_2EtNAlH_3$ in toluene at 105° C. With a Ti catalyst, this leads to the production of 80 nm particles.

In some embodiments it will be necessary to stabilize the inorganic particles, for example to prevent degradation or aggregation. Suitable capping ligands for stabilizing inorganic particles are known in the art.

Methods of Using Phase Change Nanodroplet Conjugates

Methods of using phase change nanodroplet conjugates for targeted delivery of a therapeutic, prophylactic, and/or diagnostic nanoparticles are provided. The methods can include delivery of the nanoparticle or its contents to a specific cell, tissue, organ, or organ system. The methods can include targeted delivery with little or no systemic delivery or with little or no systemic toxicity. The methods can include administering the phase change nanodroplet conjugates to a subject in need thereof and applying an effective amount of ultrasound radiation to the target region to release (e.g., cause the nanodroplet to become a gas) the nanoparticle and/or the contents of the nanoparticle at the target region. The target region can be the specific cell, tissue, organ, or organ system. The administration can include administration of the conjugates to the subject in a localized fashion, e.g. by injection or application near the target region, or by systemic administration such as orally or via injection.

In some embodiments kits are provided containing the phase change nanodroplet and the therapeutic, prophylactic, or diagnostic nanoparticle. In some embodiments the methods include attaching the nanoparticle to the outer shell of the phase change nanodroplet prior to administration. In some embodiments the methods include attaching the nanoparticle to the outer shell of the phase change nanodroplet prior to administration in the case of biological targets, but not limited to such, such as MAb. The nanoparticle and the phase change nanodroplet can be provided, for example in a kit, and the methods can include forming the conjugate prior to the administration step. For example, the nanoparticle and the phase change nanodroplet can have reacting coupling groups on the surface such that they can be reacted prior to administration to form a linker attaching the nanoparticle to the outer shell of the phase change nanodroplet.

In some embodiments the methods include targeted delivery of a therapeutic, prophylactic, or diagnostic agent across the blood brain barrier. The methods can include administering the conjugates to a subject in need thereof, e.g., administering systemically or locally via injection or intranasal administration. The methods can include applying an effective amount of ultrasound radiation to the head of the patient to stimulate the phase change nanodroplet to become a gas, thereby releasing an effective amount of the nanoparticle and/or the contents of the nanoparticle across the blood brain barrier to achieve the desired therapeutic, prophylactic, or diagnostic effect. Ultrasound power can be kept below levels that would increase the temperature of the tissue being exposed. This can be monitored in real time with MRI thermographic methods.

In some embodiments the methods include targeted delivery of a therapeutic, prophylactic, or diagnostic agent to a tumor in a subject in need thereof. The methods can include administering the conjugates to a subject in need thereof, e.g. administering systemically or locally via injection at or near the site of the tumor. The methods can include applying an effective amount of ultrasound radiation to the tumor to stimulate the phase change nanodroplet to become a gas, thereby releasing an effective amount of the nanoparticle and/or the contents of the nanoparticle at the tumor to achieve the desired therapeutic, prophylactic, or diagnostic effect.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Figure 1:
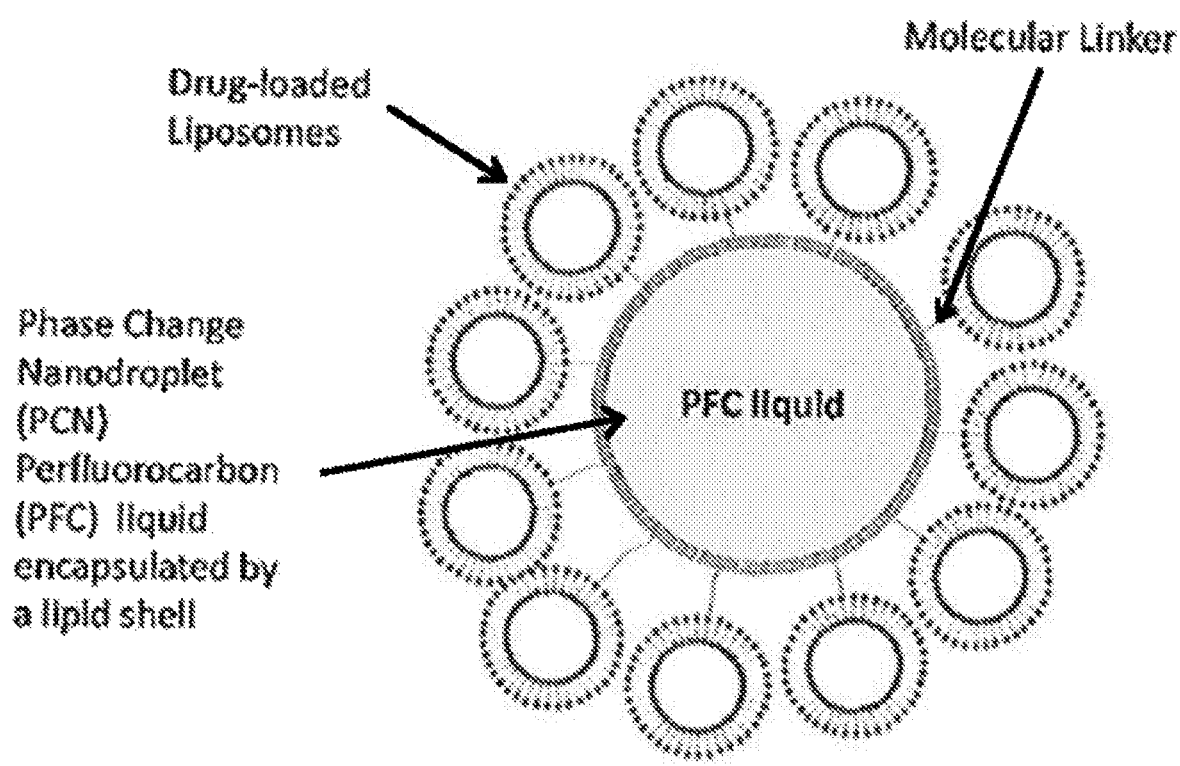
FIG. 1 is a diagram of an exemplary phase change nanodroplet conjugate having a plurality of drug loaded liposomal nanoparticles covalently attached to a phase change nanodroplet via a linker. The phase change nanodroplet has a perfluorocarbon (PFC) liquid core stabilized by an outer lipid layer.
Figures 2A, 2B:
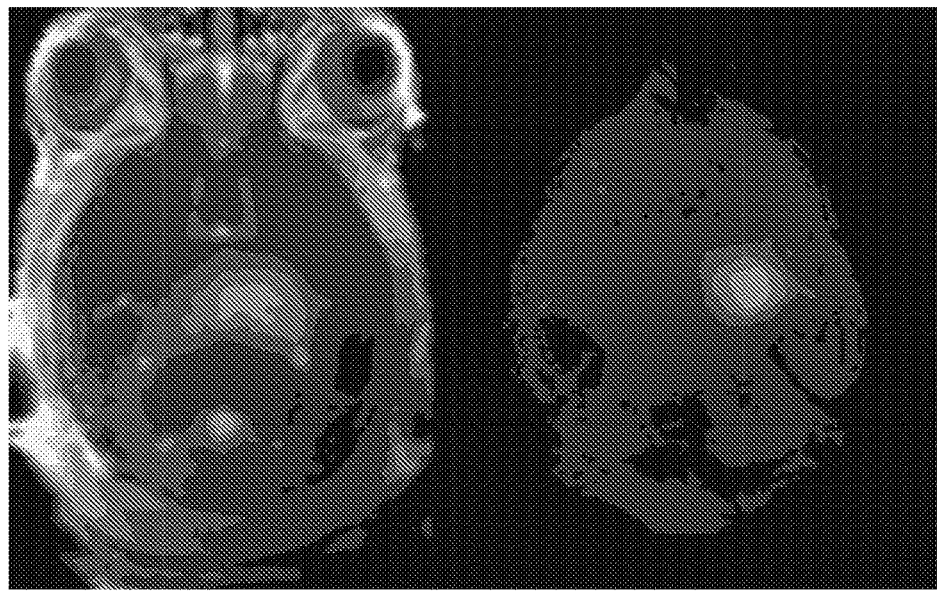
FIG. 2A is a magnetic resonance image (MRI) of the brain of an anesthetized mouse.
FIG. 2B is a fluorescence image of the mouse brain demonstrating the fluorescently labeled dextran was delivered to the brain and colocalized with the MRI signal enhancement in vivo.

One of the applications of this technology is in delivering drugs to the brain with focused ultrasound. An example of blood brain barrier opening with focused ultrasound is shown in FIGS. 2A-2B. In this experiment, an anesthetized mouse was injected IV with MRI contrast agent. This was followed by the injection of microbubbles and focused ultrasound (2.1 MHz, 0.51 mechanical index, 1% duty cycle, 2 minutes duration) was applied to the brain through the top of the skull. Magnetic resonance imaging (MRI) was carried out to validate blood brain barrier opening to the MRI contrast agent (FIG. 2A). After MRI, 1 mg of fluorescently labeled 70 kDa dextran was injected IV and allowed to circulate for 20 minutes. The mouse was then transcardially perfused with saline followed by 4% paraformaldehyde. The brain was removed, sectioned, and imaged with a fluorescence stereoscope. A representative fluorescence image is shown in FIG. 2B, indicating the delivery of the 70 kDa dextran to the brain and the co-localization with MRI signal enhancement in vivo. Delivery of drugs to other regions of the body can be carried out in a similar fashion.

Figures 3A, 3B, 3C:
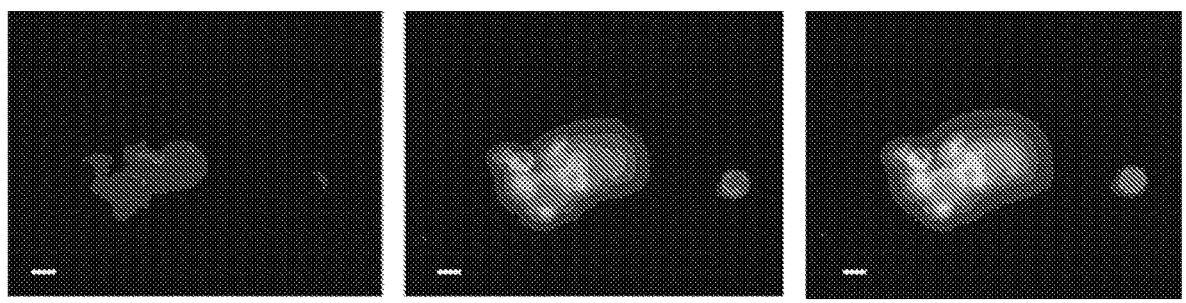
FIGS. 3A-3C demonstrate conjugation of liposomes to the lipid shell surface of a microbubble.

Making the proposed nanoparticles can include conjugating liposomes to a lipid shell surface. FIG. 3 demonstrates this capability. Lipid shelled microbubbles were synthesized and lipophilic rhodamine dye was incorporated into the lipid shell. Liposomes with a diameter of 100 nm were synthesized with carboxyfluorescein incorporated into the aqueous interior. The liposome and microbubble solutions were mixed and conjugated together. The red channel image shows the location of the rhodamine in the lipid shell. The green channel shows the location of the liposomes (too small to see individually). The merged image shows that the liposomes are conjugated to the outer shell of the microbubbles. Scale bars in the image are 1 micrometer in length.

This procedure was repeated with the substitution of nanodroplets in place of the microbubbles. Similar images are shown in FIG. 4. The nanodroplets are much smaller than the microbubbles (200-300 nanometers as opposed to 1-3 micrometer diameter) so the entire nanodroplet appears as red "dots" in the image. The co localization of the red and green colors indicates the conjugation of liposomes into the lipid shell of the nanodroplet. Scale bars in the image are 1 micrometer in length.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A phase change nanodroplet-nanoparticle conjugate comprising:
   a) a nanodroplet comprising a gaseous precursor and an encasing outer shell; and
   b) a plurality of nonmetallic nanoparticles covalently linked to the outer shell of the nanodroplet, wherein each nanoparticle comprises an encapsulated therapeutic, prophylactic, or diagnostic agent; and wherein the encapsulation is formed by noncovalent bonds.

2. The conjugate of claim 1, wherein the outer shell is a lipid monolayer, a lipid bilayer, or a polymer layer.

3. The conjugate of claim 2, wherein the outer shell comprises a lipid selected from the group consisting of a neutral lipid, a cationic lipid, an anionic lipid, a solid lipid, and a combination thereof.

4. The conjugate of claim 3, wherein the nonmetallic nanoparticle is selected from the group consisting of a polymeric particle, a lipid particle, a solid lipid particle, a liposome, and combinations thereof.

5. The conjugate of claim 1, wherein the gaseous precursor comprises one of more molecules with a boiling point of −50° C. to 10° C. at standard pressure.

6. The conjugate of claim 1, wherein the gaseous precursor comprises a straight chain or branched chain fluorocarbon, hydrofluorocarbon, or fluorohalocarbon having from 2 to 20 carbon atoms, or a combination thereof.

7. The conjugate of claim 1, wherein the gaseous precursor comprises perfluoropropane, perfluorobutane, or perfluoropentane.

8. A pharmaceutical formulation comprising the conjugate of claim 1 and a pharmaceutically acceptable excipient.

9. A method of targeted delivery of a therapeutic, prophylactic, or diagnostic nanoparticle to a target region in a subject in need thereof, the method comprising:
   administering the conjugate of claim 1.

10. The method of claim 9, further comprising applying an effective amount of ultrasound radiation to the target region to stimulate vaporization of the gaseous precursor followed by cavitation of the resultant bubble conjugate and release or dispersing of drug or drugs inside the nanoparticles.

11. The method of claim 9, wherein the target region is a specific cell, tissue, organ, or organ system.

12. The method of claim 9, wherein the target region is the brain.

13. The method of claim 9, wherein the subject has cancer and the target region is a tumor.

14. The method of claim 9 where administration is by intravenous injection.

15. The method of claim 9, wherein the effective amount of ultrasound radiation is effective to release the therapeutic, prophylactic, or diagnostic agent without damaging the target region.

16. A method of making a phase change nanodroplet-nanoparticle conjugate of claim 1, comprising reacting a first reactive coupling group on an outer shell of the nanodroplet with a second functional group on the nonmetallic nanoparticle to covalently conjugate the nonmetallic nanoparticle to the nanodroplet, wherein the nonmetallic nanoparticle comprises an encapsulated therapeutic, prophylactic, or diagnostic agent.

17. The conjugate of claim 1, wherein the nonmetallic nanoparticles comprise organic molecules.

18. The conjugate of claim 1, wherein the nonmetallic nanoparticles comprise noncovalently bonded lipid molecules.

19. The conjugate of claim 18, wherein the nonmetallic nanoparticles are liposomes encapsulating a drug.

* * * * *